(12) United States Patent
Hanson

(10) Patent No.: US 6,432,130 B1
(45) Date of Patent: Aug. 13, 2002

(54) FULLY SHEATHED BALLOON EXPANDABLE STENT DELIVERY SYSTEM

(75) Inventor: Scott M. Hanson, Savage, MN (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/552,807

(22) Filed: Apr. 20, 2000

(51) Int. Cl.$^7$ .............................. A61F 2/06; A61B 17/34
(52) U.S. Cl. ..................... 623/1.11; 606/194; 606/198
(58) Field of Search .................................. 606/198, 194, 606/195; 623/1.1, 1.11, 1.13, 1.16, 1.12, 1.15, 1.2

(56) References Cited

U.S. PATENT DOCUMENTS

| | | | |
|---|---|---|---|
| 5,158,548 A | 10/1992 | Lau et al. | 604/96 |
| 5,403,341 A | 4/1995 | Solar | 606/198 |
| 5,453,090 A | 9/1995 | Martinzez | 604/53 |
| 5,534,007 A * | 7/1996 | St. Germain et al. | 606/198 |
| 5,549,635 A | 8/1996 | Solar | 606/198 |
| 5,556,414 A * | 9/1996 | Turi | 606/198 |
| 5,628,755 A | 5/1997 | Heller et al. | 606/108 |
| 5,709,703 A | 1/1998 | Lukic et al. | 606/198 |
| 5,788,707 A | 8/1998 | Del Toro et al. | 606/198 |
| 5,810,871 A * | 9/1998 | Tuckey et al. | 606/198 |
| 5,944,726 A | 8/1999 | Blaeser et al. | 606/108 |
| 5,957,930 A * | 9/1999 | Vrba | 623/1.11 |
| 6,168,617 B1 * | 1/2001 | Blaeser et al. | 623/1.11 |

FOREIGN PATENT DOCUMENTS

| | | |
|---|---|---|
| EP | 0 732 087 | 9/1996 |
| EP | 0 990 427 A2 | 4/2000 |
| WO | 97/24080 | 6/1997 |

\* cited by examiner

*Primary Examiner*—Edward K. Look
*Assistant Examiner*—Richard Woo
(74) *Attorney, Agent, or Firm*—Vidas, Arrett & Steinkraus P.A.

(57) ABSTRACT

A stent delivery system which includes a self dividing and retracting stent retaining sleeve having a ribbed configuration. The ribbed configuration providing the sleeve with reduced columnar strength and an improved radial strength characteristics. The present stent delivery system further providing for a perforated portion on the sleeve which will rupture at a predetermined pressure thereby dividing the sleeve into a proximal portion and a distal portion. The ribbed sleeve portions providing a recoil action in opposite longitudinal directions to the individual sleeve portions which assists in actively retracting the sleeve portions off of the stent being expanded.

17 Claims, 1 Drawing Sheet

FULLY SHEATHED BALLOON EXPANDABLE STENT DELIVERY SYSTEM

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention is directed to a stent delivery system which includes a stent retaining sleeve having a ribbed configuration and a perforated portion. The unique characteristics of the present sleeve provides for a delivery system which has superior ability to in immobilize a stent on the catheter surface, and which provides the stent with the stent delivery system with improved safety and ease of use.

The sleeve of the present invention completely covers a stent mounted to a stent delivery catheter. The sleeve has sufficient strength characteristics to securely maintain a stent in its axial position on the delivery catheter, without requiring that the stent first be crimped onto the catheter surface.

It is well understood that stents which are not properly secured or retained to the catheter may slip and either be lost or be deployed in the wrong location or partially deployed. Traditionally, in order to provide proper securement of the stent on the catheter the stent is crimped to a predetermined area of the catheter.

In the past, crimping has been done by hand or by a crimping apparatus, often resulting in the application of undesired uneven forces to the stent. Such a stent must either be discarded or re-crimped. Stents which have been crimped multiple times can suffer from fatigue and may be scored or otherwise marked which can cause thrombosis. A poorly crimped stent can also damage the underlying balloon.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

The present invention avoids these problems by providing a ribbed retaining sleeve which is capable of securing a stent to the catheter without the need to crimp the stent into place. The ribbed sleeve may be utilized with nearly any type of stent. Both self-expanding and inflation expandable stents are well known and widely available in a variety of designs and configurations. Self-expanding stents must be maintained under a contained sheath or sleeve(s) in order to maintain their reduced diameter configuration during delivery of the stent to its deployment site. Inflation expandable stents are crimped to their reduced diameter about the delivery catheter, then maneuvered to the deployment site and expanded to the vessel diameter by fluid inflation. The present invention is particularly concerned with delivery and deployment of inflation expandable stents, although it is generally applicable to self-expanding stents when used with balloon catheters.

In advancing an inflation expandable stent through a body vessel to the deployment site, there are a number of important considerations. The stent must be able to securely maintain its axial position on the delivery catheter without translocating proximally or distally and especially without becoming separated from the catheter. The stent, particularly its distal and proximal ends, must be protected to prevent distortion of the stent and to prevent abrasion and/or trauma of the vessel walls.

Inflation expandable stent delivery and deployment assemblies are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Another invention which may be relevant to the present invention is disclosed in a concurrently filed and commonly assigned U.S. patent application entitled: U.S. Application entitled A NON-CRIMPED STENT DELIVERY SYSTEM, designated by U.S. patent application Ser. No. 09/553,034.

All of the references contained herein, including the co-pending Application listed above, are respectively incorporated in their entirety herein by reference.

BRIEF SUMMARY OF THE INVENTION

This invention provides for an improvement over the prior art, by providing a stent delivery system which includes a self dividing and retracting stent retaining sleeve having a ribbed configuration. The stent may be self-expanding, such as a NITINOL shape memory stent, or it may be expandable by means of an inflatable portion of the catheter, such as a balloon.

The ends of the sleeve overlap the stent and are affixed to the stent delivery catheter. The ends of the sleeve which are affixed to the catheter may be attached thereto in any manner which may be known in the art. For example: the ends may be laser or chemical welded, attached with an adhesive, utilize connection bands, etc. Preferably the sleeve has an interference fit on to the portions of the catheter shaft adjacent to the stent mounting region. The ribbed configuration of the sleeve provides the sleeve with a reduced columnar strength while simultaneously providing radial strength characteristics sufficient to retain and immobilize a non-crimped stent on the catheter surface.

The ribbed configuration of the sleeves provides a plurality of alternating raised and lowered pleats, with the lowered pleats contacting the stent. The sleeve may be composed of an elastic polymer, a non-elastic polymer or any combination thereof.

The reduced columnar strength of the sleeve is at least in part a consequence of having only the downward pleats of the sleeve ribbing, rather than the entire internal surface of the sleeve, frictionally engaging the stent surface. The reduced columnar strength provided by this arrangement allows the sleeve to be readily retracted from the surface of the stent. Preferably, the sleeve has sufficiently low frictional interface with the stent so as to not require the application of a lubricant. Alternatively, the sleeve may be pre-lubricated.

The sleeve includes a perforated portion which splits and divides the sleeve into proximal and distal portions during expansion of the stent. The ribbed configuration of the sleeve further provides a spring or recoil action to the proximal and distal sleeve portions. The recoil action of each sleeve is directed in longitudinally opposing directions and assists in actively retracting the sleeve portions off of the stent in the appropriate direction. When the stent is expanded and the sleeve is split, the recoil action will retract the divided portions of the sleeve toward the respective ends (proximal and distal) of the sleeve which are attached to the catheter. The rupturing of the perforated section of the sleeve, the recoil action and the reduced columnar strength of the sleeve combine to allow the sleeve portions to be pulled completely off of the stent with improved effectiveness.

The ribbed configuration also provides the sleeve with radial strength characteristics sufficient to provide an interference fit between the sleeve and the stent. The interference fit retains the sleeve in a desired position and in a reduced configuration until the recoil action is triggered by the expansion of the stent and the rupture of the sleeve. The radial strength characteristics of the ribbed sleeve portions are such that even during the retraction of the sleeve portions the interference fit is maintained, thus providing a uniform and consistent retraction of the sleeve portions while also ensuring that the retracted sleeve portions remain reduced and thus, do not interfere with the safe removal of the catheter from the vessel subsequent to stent delivery.

The present invention provides for a sheath or sleeve which may completely encompass a stent on the stent delivery catheter, and which may be removed from the stent without the need to employ a retraction wire or member. By providing a sleeve which may cover the entire stent the present invention helps to ensure that the stent is completely immobilized on the catheter surface. In addition, by completely containing a stent within the sleeve the potential for vessel wall damage during the advancement of the catheter is minimized.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
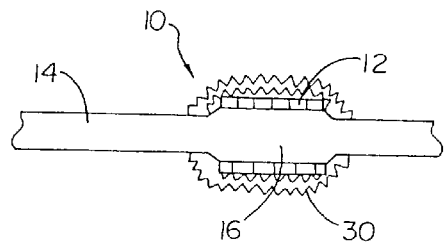
FIG. 1 is a perspective view of the stent delivery system showing the ribbed sleeve in place over the stent in the unexpanded position.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

FIG. 1 shows a first embodiment of a stent delivery system, indicated generally at 10, which includes a stent 12 is mounted upon a stent delivery catheter 14. FIG. 1 shows the stent delivery system prior to stent delivery. A stent retaining sleeve 30 is employed to retain the stent 12 on an inflatable portion 16 of the delivery catheter 14 prior to stent delivery.

Stent 12 is placed on the delivery catheter 14 by placing the stent on a stent mandril and reducing the stent to a diameter sufficient for mounting the stent on the catheter. It is not necessary to crimp the stent on to the catheter, but if desired the stent may be crimped. As previously indicated, the present invention provides for stent retaining sleeve 30 which have sufficient radial strength to retain a reduced, but non-crimped stent on the delivery catheter.

Figure 2:
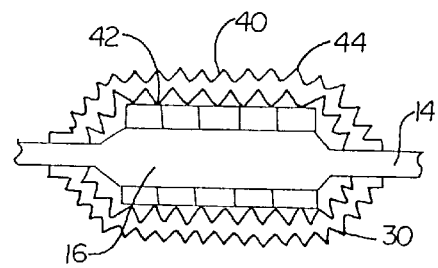
FIG. 2 is a close-up view of the sleeve showing the alternating raised and lowered pleats.

As may best be seen in FIG. 2, the sleeve 30 has ribbed portions 40 which may be characterized as being made up of a plurality of folds or pleats which have been pressed into the sleeve material. The pleats are comprised of alternating lower pleats 42 and raised pleats 44. The sleeve 30 is preferably constructed from polyurethane such as Techothane® 1055D produced by Thermedics Inc. located in Woburn, Mass. Other materials may be alternatively or additionally used, such as: elastic polymers, non-elastic polymers and any combinations thereof. The pleats 42 and 44 are formed by swelling an extruded tube and then shrinking the tube over a mandrel with the desired pleat configuration. The tube is then heat set on the mandrel. Finally, the heat seated pleated sleeve is expanded off of the mandrel. A perforated or weakened portion 32 of the sleeve 30 may be formed as a result of surface features on the mandrel, alternatively the perforated portion 32 may be formed by cutting, abrading or thinning out predetermined areas of the sleeve 30 thereby forming perforations 36. Between perforations 36 is positioned the remaining sleeve material, referred to as bridge material 34.

Figure 3:
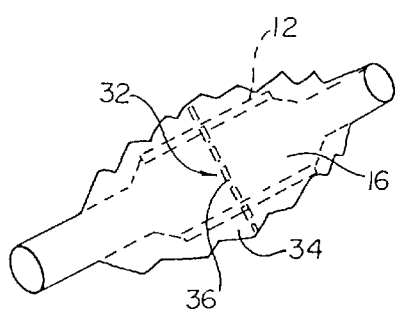
FIG. 3 is a perspective view of the stent delivery system of FIG. 1 shown during the initial expansion of the stent prior to the rupture of the sleeve.
Figure 4:
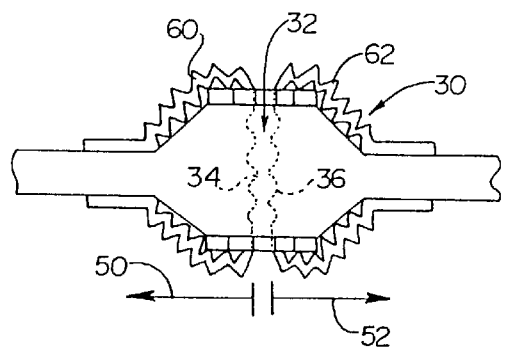
FIG. 4 is a perspective view of the stent delivery system of FIG. 1 shown during stent expansion and retraction of the sleeve portions.

As may be seen in FIG. 3, when the stent 12 is initially expanded by inflation of the inflatable portion 16, the initial expansion of the stent places a radially outward pressure on the perforated portion 32 of the sleeve 30. As the stent 12 expands, the bridge material 34, which separate the perforations 36, will begin to stretch outward both radially and longitudinally. At a predetermined pressure, the bridge material 34 will break or snap resulting in the sleeve 30 rupturing into a proximal portion 60 and a distal portion 62, as seen in FIG. 4. Preferably, the bridge material 34 will break and the pleats 40 and 42 will retract when the inflatable portion 16 is expanded under a pressure of approximately 6 atmospheres. The pressure may vary in alternative embodiments.

It should be noted that in addition to the position of the perforated portion 32 shown in the embodiment described herein, the perforated portion 32 may be located anywhere on the sleeve 30 as desired and is not limited to the substantially central position presently shown.

Prior to and during expansion of the stent 12, only the lower pleats 42 are in contact with the surface of the stent. By providing a ribbed sleeve 30 and sleeve portions 60 and 62 which contact the stent surface in such a limited manner, the sleeve 30 will have a reduced frictional engagement against the stent 12. This reduced frictional engagement translates functionally to the sleeve 30 having a reduced columnar strength. As a result, the sleeve portions may be retracted from the stent with no need to have a supplemental lubricant added between the stent and sleeves.

In addition to the reduced columnar strength provided by the ribbed configuration of the sleeve 30, the ribbed configuration assists in ready retraction of the sleeve portions from the stent by providing the sleeves with a recoil action. As may be seen in FIG. 2, the pleats 42 and 44 provide the sleeve 30 with a zig-zag pattern much like that of a spring. This pattern of alternating pleats provides the sleeve with a tension force in longitudinally opposing directions as described below.

In the embodiment shown in FIG. 4, the tension force is exerted in the proximal direction and the distal direction as indicated by arrows 50 and 52. The combination of the tension force and the reduced columnar strength provided to the sleeve by the ribbed configuration, as well as the act of snapping the bridge material 34 combine to cause the proximal sleeve portion 60 to actively retract off of the stent 12 in the proximal direction and the distal sleeve portion 62 to actively retract off of the stent 12 in the distal direction.

It may be desirable to have one end of the stent freed sooner than the other end, the individual sleeve portions 60 and 62 may be configured to have the same or different retraction rates by altering the individual sleeve portion's composition, diameter and/or pleat arrangement. The order in which the sleeve portions are retracted off of the stent may also be affected by the position of the perforated portion.

Figure 5:
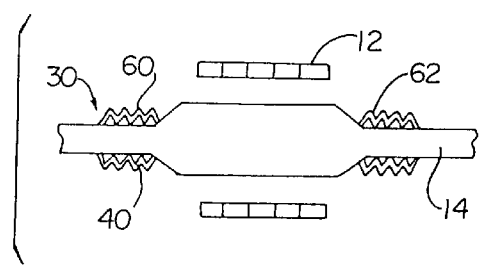
FIG. 5 is a perspective view of the stent delivery system of FIG. 1 shown after the stent is fully expanded.

In FIG. 5 stent 12 is shown in the expanded, delivered state. In order to properly deliver stent 12, the sleeve portions 60 and 62 must be fully retracted off of stent ends 20 and 22. Prior to expansion of stent 12, the sleeve 30 and later the sleeve portions 60 and 62, provide an inward radial force sufficient to immobilize the stent on catheter 14 and to retain the non-crimped stent in the unexpanded state, such as may be seen in FIG. 1. The radial force provided by the sleeve 30 is maintained during the retraction of sleeve portions 60 and 62, and even after the portions are fully removed from stent 12. As a result the portions 60 and 62 will tend to collapse upon themselves and maintain the relatively low profile of catheter 14 despite the added relative height of the compacted ribbing 40.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery system comprising:
    a stent delivery catheter, the stent delivery catheter having a stent mounting region, the stent mounting region including a stent inflation balloon;
    a stent disposed about the stent mounting region, the stent having an unexpanded state and being pressure expandable to a fully expanded state;
    a retaining sleeve, the retaining sleeve includes proximal and distal end sections and a center section, at least a portion of the proximal and distal end sections being fixedly engaged to the catheter, at least a portion of the central section having a pleated configuration, the retaining sleeve retaining and immobilizing the stent in the unexpanded state on the stent delivery catheter, the central section having a central proximal section and a central distal section joined together by a structurally weakened section of the retaining sleeve, such that when the balloon is expanded the structurally weakened section ruptures separating the central proximal section form the central distal section, the central proximal section and the central distal section respectively collapsing toward the fixedly engaged proximal end section and the distal end section as the stent is expanded to the fully expanded state.

2. The stent delivery system of claim 1 wherein the pair of end portions have a pleated configuration.

3. The stent delivery system of claim 1 wherein the pair of end portions provide retraction tension on the proximal section and the distal section.

4. The stent delivery system of claim 1 wherein the weakened section is defined by a plurality of perforations between the proximal section and the distal section.

5. The stent delivery system of claim 1 wherein the stent mounting region is defined by one or more radiopaque marker bands.

6. The stent delivery system of claim 1 wherein the stent is not crimped.

7. The stent delivery device of claim 1 wherein the sleeve is constructed from at least one member of the group essentially consisting of polyurethane, elastic polymers, non-elastic polymers and any combinations thereof.

8. A method of manufacturing the sleeve of claim 7 comprising the steps of:
    (a) extruding a tube of elastic material;
    (b) swelling the extruded tube;
    (c) shrinking the extruded tube over a mandrel, the mandrel having an outside surface characterized as being pleated, the outside surface providing the extruded tube with the pleated configuration;
    (d) heat setting the tube while it is in place on the mandrel; and
    (e) swelling the heat set tube off of the mandrel.

9. The method of claim 8 further comprising the step of: weakening a portion of the tube.

10. The method of claim 9 wherein the weakening is created by forming perforations in the portion of the tube.

11. The method of claim 10 wherein the perforations are formed as a result of surface features of the mandrel.

12. The method of claim 8 wherein the elastic material is selected from at least one member of the group essentially consisting of polyurethane, elastic polymers, non-elastic polymers and any combinations thereof.

13. A sleeve having sufficient radial compression to retain a stent in an unexpanded state on a stent delivery catheter and further having columnar strength characteristics sufficient to provide the sleeve with the ability to be readily withdrawn from the stent comprising:
    a proximal end and a distal end, the ends constructed and arranged to engage a stent delivery catheter;
    a central portion, at least the central portion having a pleated configuration, the central portion constructed and arranged to be disposed about the stent in the unexpanded state, the central portion constructed and arranged to separate into a proximal section and a distal section when a predetermined pressure is applied to the central portion, the proximal section constructed and arranged to be drawn off of the stent toward the proximal end, the distal section constructed and arranged to be drawn off of the stent toward the distal end.

14. The sleeve of claim 13 wherein the predetermined pressure is approximately 6 atmospheres.

15. The sleeve of claim 13 wherein the predetermined pressure is characterized as a uniform radial pressure from within the sleeve.

16. The sleeve of claim 13 wherein the ends are further constructed and arranged to engage the catheter by an interference fit.

17. The sleeve of claim 13 wherein the stent is not crimped.

* * * * *